(12) United States Patent
Kaddurah-Daouk

(10) Patent No.: US 7,186,754 B2
(45) Date of Patent: Mar. 6, 2007

(54) USE OF CREATINE OR CREATINE COMPOUNDS FOR SKIN PRESERVATION

(75) Inventor: Rima Kaddurah-Daouk, Belmont, MA (US)

(73) Assignee: Avicena Group, Inc., Palo Alto, CA (US)

( * ) Notice: Subject to any disclaimer, the term of this patent is extended or adjusted under 35 U.S.C. 154(b) by 0 days.

(21) Appl. No.: 11/088,519

(22) Filed: Mar. 23, 2005

(65) Prior Publication Data

US 2005/0227996 A1 Oct. 13, 2005

Related U.S. Application Data

(63) Continuation of application No. 09/852,966, filed on May 10, 2001, which is a continuation of application No. 09/344,427, filed on Jun. 25, 1999, now Pat. No. 6,242,491.

(51) Int. Cl.
*A61K 31/195* (2006.01)
*A61K 31/19* (2006.01)
*A61K 6/00* (2006.01)
*A61K 8/02* (2006.01)

(52) U.S. Cl. ............... 514/565; 514/557; 514/859; 514/861; 514/864; 424/401; 424/642; 424/423

(58) Field of Classification Search ............... 514/565, 514/557, 859, 861, 864; 424/401, 642, 423
See application file for complete search history.

(56) References Cited

U.S. PATENT DOCUMENTS

| | | | |
|---|---|---|---|
| 3,989,816 A | 11/1976 | Rajadhyaksha | |
| 4,017,641 A | 4/1977 | DiGiulio | |
| 4,130,667 A | 12/1978 | Smith | |
| 4,254,105 A | 3/1981 | Fukuda | |
| 4,537,776 A | 8/1985 | Cooper | |
| 4,552,872 A | 11/1985 | Cooper et al. | |
| 4,557,934 A | 12/1985 | Cooper | |
| 4,599,379 A | 7/1986 | Flesher et al. | |
| 4,628,078 A | 12/1986 | Glover et al. | |
| 4,663,157 A | 5/1987 | Brock | |
| 4,772,591 A | 9/1988 | Meisner | |
| 4,847,069 A | 7/1989 | Bissett et al. | |
| 4,847,071 A | 7/1989 | Bissett et al. | |
| 4,891,227 A | 1/1990 | Thaman et al. | |
| 4,891,228 A | 1/1990 | Thaman et al. | |
| 4,912,248 A | 3/1990 | Mueller | |
| 4,960,764 A | 10/1990 | Figueroa, Jr. et al. | |
| 5,091,171 A * | 2/1992 | Yu et al. ............ | 424/642 |
| 5,091,404 A | 2/1992 | Elgebaly | |
| 5,321,030 A | 6/1994 | Kaddurah-Daouk et al. | |
| 5,324,731 A | 6/1994 | Kaddurah-Daouk et al. | |
| 5,385,938 A * | 1/1995 | Yu et al. ............ | 514/557 |
| 5,599,841 A | 2/1997 | Meglasson | |
| 5,674,703 A | 10/1997 | Woo et al. | |
| 5,676,978 A | 10/1997 | Teicher et al. | |
| 5,702,688 A | 12/1997 | Yu et al. | |
| 5,723,133 A | 3/1998 | Nagai et al. | |
| 5,834,513 A * | 11/1998 | Ptchelintsev et al. ....... | 514/561 |
| 5,847,003 A | 12/1998 | Ptchelintsev et al. | |
| 5,883,128 A | 3/1999 | Yu et al. | |
| 5,886,041 A | 3/1999 | Yu et al. | |
| 5,912,272 A | 6/1999 | Hoppe et al. | |
| 5,925,378 A | 7/1999 | Carnazzo | |
| 5,939,078 A | 8/1999 | Fujimura et al. | |
| 5,989,583 A * | 11/1999 | Amselem ................ | 424/439 |
| 6,069,169 A | 5/2000 | Ptchelintsev et al. | |
| 6,071,962 A | 6/2000 | Ptchelintsev et al. | |
| 6,168,802 B1 | 1/2001 | Howard et al. | |
| 6,242,491 B1 * | 6/2001 | Kaddurah-Daouk ........ | 514/565 |
| 6,261,575 B1 | 7/2001 | Hoppe et al. | |
| 6,277,881 B1 | 8/2001 | Santhanam et al. | |
| 6,333,356 B1 | 12/2001 | Ptchelintsev et al. | |
| 6,338,855 B1 | 1/2002 | Albacarys et al. | |
| 6,413,552 B1 | 7/2002 | Stoll | |
| 6,479,069 B1 * | 11/2002 | Hamilton ................ | 424/439 |
| 6,524,611 B2 | 2/2003 | Howard et al. | |
| 6,730,331 B1 | 5/2004 | Stoll | |
| 6,767,924 B2 | 7/2004 | Yu et al. | |

(Continued)

FOREIGN PATENT DOCUMENTS

EP 0043738 B1 1/1982

(Continued)

OTHER PUBLICATIONS

Ames, Bruce N. et al, "Oxidants, antioxidants, and the degerative diseases of aging," *Proc. Natl. Acad. Sci. USA*, vol. 90:7915-7922 (1993).

(Continued)

*Primary Examiner*—Vickie Kim
(74) *Attorney, Agent, or Firm*—Avicena & Cockfield, LLP; Elizabeth A. Hanley; Cynthia M. Soroos

(57) ABSTRACT

The present invention relates to the use of creatine compounds such as, for example, creatine, creatine phosphate or analogs of creatine, such as creatine-pyruvate, creatine-ascorbate, cyclocreatine, 3 guanidinopropionic acid, guanidinoacetate, homocyclocreatine, guanidino benzoates as energy generating systems and antioxidants for preservation of skin against adverse aging effects and damage secondary to insults such as harmful sun radiations, stress and fatigue. The creatine compounds which can be used in the present method include (1) creatine, creatine phosphate and analogs of these compounds which can act as substrates or substrate analogs for creatine kinase; (2) molecules that mimic the biological activity of creatine (3) molecules that modulate the creatine kinase system.

11 Claims, 4 Drawing Sheets

U.S. PATENT DOCUMENTS

| | | | |
|---|---|---|---|
| 2002/0044913 | A1 | 4/2002 | Hamilton |
| 2002/0049253 | A1 | 4/2002 | Kaddurah-Daouk |
| 2004/0029969 | A1 | 2/2004 | Blatt et al. |
| 2004/0052749 | A1 | 3/2004 | Golz-Berner et al. |
| 2004/0092482 | A1 | 5/2004 | Gupta |
| 2004/0161435 | A1 | 8/2004 | Gupta |
| 2004/0208902 | A1 | 10/2004 | Gupta |
| 2004/0219124 | A1 | 11/2004 | Gupta |
| 2004/0228884 | A1 | 11/2004 | Gupta |
| 2004/0241197 | A1 | 12/2004 | Biergiesser et al. |
| 2004/0258717 | A1 | 12/2004 | Suermann et al. |
| 2005/0186158 | A1 | 8/2005 | Kaddurah-Daouk |
| 2005/0186194 | A1 | 8/2005 | Kaddurah-Daouk |
| 2005/0226840 | A1 | 10/2005 | Kaddurah-Daouk |
| 2005/0227996 | A1 | 10/2005 | Kaddurah-Daouk |

FOREIGN PATENT DOCUMENTS

| | | |
|---|---|---|
| EP | 0413528 A1 | 2/1991 |
| EP | 0465756 A1 | 1/1992 |
| EP | 0500332 B1 | 8/1992 |
| EP | 0565010 A1 | 10/1993 |
| EP | 0852949 A2 | 7/1998 |
| GB | 817749 | 8/1959 |
| GB | 2103605 | 2/1983 |
| GB | 2357970 | 7/2001 |
| JP | 06-192085 | 7/1994 |
| JP | 09-202710 | 5/1997 |
| JP | 2000-247866 | 9/2000 |
| JP | 2001-114701 | 4/2001 |
| WO | WO-90/09192 A1 | 8/1990 |
| WO | WO-92/08456 A2 | 5/1992 |
| WO | WO-94/16687 A1 | 8/1994 |
| WO | WO-95/26182 A1 | 10/1995 |
| WO | WO-96/14063 A1 | 5/1996 |
| WO | WO-97/12591 A1 | 4/1997 |
| WO | WO-97/17056 A1 | 5/1997 |
| WO | WO-97/41848 A1 | 11/1997 |
| WO | WO-97/42960 A1 | 11/1997 |
| WO | WO-97/46231 A1 | 12/1997 |
| WO | WO-98/28263 A1 | 7/1998 |
| WO | WO-99/55302 A1 | 11/1999 |
| WO | WO-99/55303 A1 | 11/1999 |
| WO | WO-00/15187 A1 | 3/2000 |
| WO | WO-00/40217 A1 | 7/2000 |
| WO | WO-01/01932 A2 | 1/2001 |
| WO | WO-02/060394 A2 | 8/2002 |
| WO | WO-03/005988 A1 | 1/2003 |

OTHER PUBLICATIONS

Bessman, Samuel P., "The Creatine-Creatine Phosphate Energy Shuttle," *Ann. Rev. Biochem.*, vol. 54:831-862 (1982).

Cutler, Adrian J. et al, "Properties of a Microsomal Enzyme System from *Linum usitatissimum* (Linen Flax) Which Oxidizes Valine to Acetone Cyanohydrin and Isoleucine to 2-Methylbutanone Cyanohydrin," *Archives of Biochemistry and Biophysics*, vol. 238(1):272-279 (1985).

Davies, Joanna M.S. et al, "Transient Adaptation to Oxidative Stress in Yeast," *Archives of Biochemistry and Biophysics*, vol. 317(1):1-6 (1995).

Harman, Denham, "Free radicals in aging," *Molecular and Cellular Biochemistry*, vol. 84:155-161 (1988).

O'Gorman, Eddie et al, "The role of creatine kinase in inhibition of mitochondrial permeability transition," *FEBS*, vol. 414:253-257 (1997).

Sohal, Rajindar S. et al, "Oxidative Stress, Caloric Restriction, and Aging," *Science*, vol. 273:59-63 (1996).

Sohal, Rajindar S. et al, "Oxidative stress and aging in the Mongolian gerbil (*Meriones unguiculatus*)," *Mechanisms of Ageing and Development*, vol. 81:15-25 (1995).

Stadtman, Earl R., "Protein Oxidation and Aging," *Science*, vol. 257:1220-1224 (1992).

Wallimann, Theo et al, "Intracellular compartmentation, structure and function of creatine kinase isoenzymes in tissues with high and fluctuating energy demands: the 'phosphocreatine circuit' for cellular energy homeostasis," *Biochem. J.*, vol. 281:21-40 (1992).

Weindruch, Richard, "Interventions Based on the Possibility That Oxidative Stress Contributes to Sarcopenia," *The Journals of Gerontology Series A*, vol. 50A(Special Issue):157-161 (1995).

Wyss, Markus et al, "1-4 Creatine metabolism and the consequences of creatine depletion in muscle," *Molecular and Cellular Biochemistry*, vol. 133/134:51-66 (1994).

Cuono, Charles, B. et al, "Critical Role of Phosphagens in the Energy Cascade of Cutaneous Ischemia and Protective Action of Phosphocreatine Analogues in Skin Flap Survival," *Plastic and Reconstructive Surgery*, vol. 101(6):1597-1603 (1998).

Declercq, Lieve et al, "Age-dependent response of energy metabolism of human skin to UVA exposure: an *in vivo* study by $^{31}$P nuclear magnetic resonance spectroscopy," *Skin Research and Technology*, vol. 8:125-132 (2002).

Lenz, Holger et al, "The Creatine Kinase System in Human Skin: Protective Effects of Creatine Against Oxidative and UV Damage *In Vitro* and *In Vivo*," *The Journal of Investigative Dermatology*, vol. 124(2):443-452 (2005).

Schlattner, Uwe et al, "Creatine Kinase and Creatine Transporter in Normal, Wounded, and Diseased Skin," *J. Invest. Dermatol.*, vol. 118:416-423 (2002).

Zemtsov, A., "A Measurement of suberythema UVA radiation effects on skin by $^{31}$P magnetic resonance spectroscopy," *Photodermatology, Photoimmunology & Photomedicine*, vol. 13:24-26 (1997).

* cited by examiner

USE OF CREATINE OR CREATINE COMPOUNDS FOR SKIN PRESERVATION

RELATED APPLICATIONS

This application is a continuation of U.S. application Ser. No. 09/852,966, filed on May 10, 2001, which is a continuation of U.S. Ser. No. 09/344,427, filed on Jun. 25, 1999 (now U.S. Pat. No. 6,242,491 B1, issued on Jun. 5, 2001); the entire contents of each of the aforementioned applications are hereby incorporated herein by reference.

Creatine and creatine compounds are discussed in related applications including U.S. patent application Ser. No. 08/853,174, filed on May 7, 1997; U.S. patent application Ser. No. 08/914,887, filed on Aug. 19, 1997; U.S. patent application Ser. No. 08/736,967, filed on Oct. 25, 1996; and U.S. patent application Ser. No. 09/285,395, filed on Apr. 2, 1999. The entire contents of each of the applications, including all references cited therein, and hereby expressly incorporated herein by reference.

BACKGROUND OF THE INVENTION

The creatine kinase/creatine phosphate energy system is only one component of an elaborate energy-generating system found in tissue with high and fluctuating energy requirements. The components of the creatine energy system include the enzyme creatine kinase, the substrates creatine and creatine phosphate, and the transporter of creatine. The reaction catalyzed by creatine kinase is: $MgADP+PCr^=+H^+$ $MGATP^=+Cr$. Some of the functions associated with this system include efficient regeneration of energy in cells with fluctuating and high energy demands, energy transport to different parts of the cell, phosphoryl transfer activity, ion transport regulation, and involvement in signal transduction pathways.

Creatine is a compound which is naturally occurring and is found in mammalian brain and other excitable tissues, such as skeletal muscle, retina and heart. Its phosphorylated form, creatine phosphate, also is found in the same organs and is the product of the creatine kinase reaction utilizing creatine as a substrate. Creatine phosphate is one of the highest energy generating compounds in the cell and creatine is an excellent stimulant of oxidative phosphorylation and high energy production. Creatine has been extensively used by body builders as a means of stimulating energy production in the skeletal muscle. Creatine and creatine phosphate can be synthesized relatively easily and are believed to be non-toxic to mammals. Creatine, creatine phosphate and the enzymes that utilize them as substrates, i.e. the creatine kinases represent an efficient system for the rapid regeneration of energy. Kaddurah-Daouk et al. (WO 92/08456 published May 29, 1992 and WO 90/09192, published Aug. 23, 1990; U.S. Pat. No. 5,321,030; and U.S. Pat. No. 5,324,731) describe methods of inhibiting the growth, transformation and/or metastasis of mammalian cells using related compounds. Examples of compounds described by Kaddurah-Daouk et al. include cyclocreatine, b-guandidino propionic acid, homocyclocreatine, 1-carboxymethyl-2-iminohexahydropyrimidine, guanidino acetate and carbocreatine. These same inventors have also demonstrated the efficacy of such compounds for combating viral infections (U.S. Pat. No. 5,321,030). Elebaly in U.S. Pat. No. 5,091,404 discloses the use of cyclocreatine for restoring functionality in muscle tissue. Cohn in PCT publication No. WO94/16687 described a method for inhibiting the growth of several tumors using creatine and related compounds. Kaddurah-Daouk et. al. (WO 96/14063) reported on the neuroprotective effect of creatine compounds especially against neurodegenerative diseases such as Huntington's, Parkinson's, ALS, Alzheimer's.

Aging involves death of cells or cell dysfunction due to production of free radicals, oxidative damage and energy depletion due to mitochondrial dysfunction. Harman (1988) linked senescence or death to the injurious effects of free radicals arising from the one-electron reduction of oxygen during metabolism. There has been an inverse relationship between auto-oxidation rate in different animal species and life expectancy in the same species (Cutler 1985; Sohal 1995). Mitochondria are the major source of oxygen radicals through the respiratory chain and are also deeply affected by reactive oxygen species (ROS), resulting in serious risks to their function. Mitochondrial dysfunction could result in defects in electron transport, oxidative phosphorylation and energy production resulting in cell damage and ultimately cell death.

SUMMARY OF THE INVENTION

The present invention relates to methods for protecting skin tissue against age related damage or insults such as harmful UV radiation, stress and fatigue by preserving energy pools and protecting against free radical production and oxidative stress. This is achieved by administering an amount of a creatine compound or compounds which modulate one or more of the structural or functional components of the creatine kinase/phosphocreatine system sufficient to prevent, reduce or ameliorate skin damage or skin aging. Compounds which are effective for this purpose include the natural compound creatine in its different hydration or salt forms and analogs of creatine. The compounds can be mixed in with creams, oils, emulsions and the like to be spread readily on skin surfaces. Alternatively, the compounds also can be packaged in a supplement form.

The present invention also provides compositions containing creatine compounds in combination with a pharmaceutically or cosmetically acceptable carrier, and effective amounts of other agents which act on tissue preservation such as antioxidants (e.g., CoQ10), vitamins such as C, B5,B6,B9, E, energy enhancing agents (for example ATP, pyruvate, nicotinamide) and skin softeners to slow the process of aging.

Packaged formulations for preventing or slowing the process of aging also are the subject of the present invention. The packaged formulations include a container holding the creatine compound, in combination with a pharmaceutically or cosmetically acceptable carrier, along with instructions for administering the same for the purpose of preventing, ameliorating, arresting or eliminating the process of skin aging or skin damage.

DETAILED DESCRIPTION OF THE INVENTION

Figure 1:
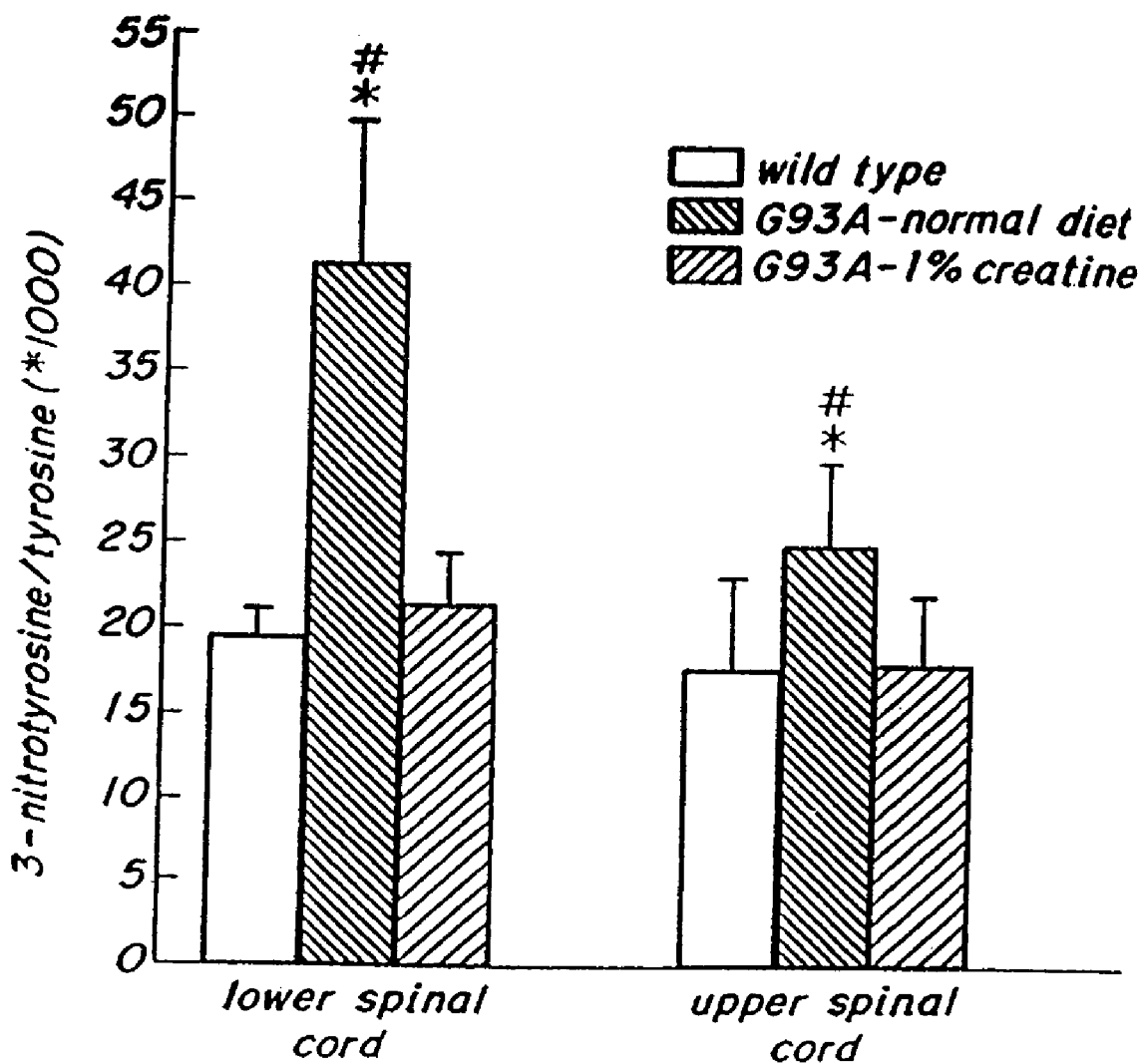
FIG. 1 depicts the effects of 1% creatine supplementation on 3-nitrotyrosine/tyrosine concentration in FALS mice. Animals were placed on 1% creatine at age 70 days and levels of 3-nitrotyrosine/tyrosine concentrations were determined at age 120 days. White column represents wild type mice, black G93A transgenic mice fed a normal diet and the dark gray column represents G93A transgenic mice fed a 1% creatine diet. *p is less than 0.05 compared with littermate controls; #p less than 0.05 compared with creatine supplementation.

The methods of the present invention generally comprise administering to a subject an amount of a creatine compound or compounds. It is thought that the creatine compounds modulate one or more of the structural or functional components of the creatine kinase/phosphocreatine system sufficient to prevent, reduce or ameliorate symptoms of aging and damage to the skin. Components of the system which can be modulated include the enzyme creatine kinase, the substrates creatine and creatine phosphate, and the transporter of creatine. The term "modulate," "modulation" or "modulating" includes any increase or decrease in the activity of any component of the creatine kinase/phosphocreatine system.

In one embodiment, the invention pertains to a method for treating a subject (e.g., a mammal, preferably, a human) for skin disorders by administering to the subject an effective amount of a creatine compound such that the skin damage is treated.

The term "mammal" includes any animal which may be treated by the compositions of the invention. Examples of mammals include dogs, cats, horses, pigs, cows, rodents, horses, bears, monkeys, gorillas, chimpanzees, and, preferably, humans.

Creatine compounds are predicted to preserve tissue by boosting up energy reserves in the skin and also by arresting mechanisms involved in oxidative damage and cell death. Compounds which are particularly effective for this purpose include creatine, creatine phosphate, and analogs thereof which are described in detail below. The term "creatine compounds" includes creatine, creatine phosphate, and compounds which are structurally similar to creatine or creatine phosphate, and analogs of creatine and creatine phosphate. The term "creatine compounds" also includes compounds which "mimic" the activity of creatine, creatine phosphate or creatine analogs. The term "mimics" is intended to include compounds which may not be structurally similar to creatine but mimic the therapeutic activity of creatine, creatine phosphate or structurally similar compounds. Also the term creatine compound includes "modulators of the creatine kinase system," for example, compounds which modulate the activity of the enzyme, or the activity of the transporter of creatine or the ability of other proteins or enzymes or lipids to interact with the system.

The term "treatment" includes the diminishment or alleviation of at least one symptom associated or caused by the disorder being treated. For example, treatment can be diminishment of several symptoms of a disorder or complete eradication of a disorder.

The language "treating for skin disorders" includes both prevention of disorders, amelioration and/or arrest of the disorder process. Examples of skin disorders include, but are not limited to aging and damage resulting from sun radiation, stress, fatigue and/or free radicals. Although not wishing to be bound by theory, the creatine compounds described herein are thought to have both curative and prophylactic effects on development of damage and aging of the skin and other tissue. The language also includes any amerlioration or arrest of any symptoms associated with the disorder process (e.g., wrinkles). For example, treating wrinkles may include preventing, retarding, arresting, or reversing the process of wrinkle formation in skin, e.g., mammalian skin, preferably, human skin.

In a further embodiment, the method includes coadministration of the creatine compound with a pharmaceutically acceptable carrier. Preferably, the pharmaceutically acceptable carrier is suitable for topical administration.

The term "topical administration" includes methods of delivery such as laying on or spreading on the skin. It involves any form of administration which involves the skin. Examples of compositions suitable for topical administration, include but are not limited to, ointments, lotions, creams, cosmetic formulations, and skin cleansing formulations. Additional examples include aerosols, solids (such as bar soaps) and gels.

The term "pharmaceutically acceptable" includes drugs, medicaments or inert ingredients which are suitable for use in contact with the tissues of humans and lower animals without undue toxicity, incompatibility, instability, irritation, allergic response, and the like, commensurate with a reasonable benefit/risk ratio. The term also encompasses cosmetically acceptable ingredients.

The language "therapeutically or cosmetically effective amount" is intended to include the amount of the creatine compound sufficient to prevent onset of aging or damage to the skin or significantly reduce progression of damage in the subject being treated. A therapeutically or cosmetically effective amount can be determined on an individual basis and will be based, at least in part, on consideration of the severity of the symptoms to be treated and the activity of the specific analog selected if an analog is being used. Further, the effective amounts of the creatine compound may vary according to the age of the subject being treated. Thus, a therapeutically or cosmetically effective amount of the creatine compound can be determined by one of ordinary skill in the art employing such factors as described above using no more than routine experimentation in health care management.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can performs its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; fruit acids, pyrogen-free water; isotonic saline; Ringer's solution; ethyl alcohol; phosphate buffer solutions; and other non-toxic compatible substances employed in pharmaceutical formulations.

The topical pharmaceutical compositions of the present invention may be made into a wide variety of product types. These include, but are not limited to solutions, lotions, creams, beach products, gels, sticks, sprays, pads, ointments, pastes, mousses and cosmetics. These product types may comprise several types of carrier systems including, but not limited to solutions, emulsions, gels and solids.

The topical pharmaceutical compositions of the present invention formulated as solutions typically include a pharmaceutically-acceptable aqueous or organic solvent. The terms "pharmaceutically-acceptable aqueous solvent" and "pharmaceutically-acceptable organic solvent" refer to a solvent which is capable of having dispersed or dissolved therein the active compound, and possesses acceptable safety properties (e.g., irritation and sensitization characteristics). Water is a typical aqueous solvent. Examples of suitable organic solvents include: propylene glycol, butylene glycol, polyethylene glycol (200–600), polypropylene glycol (425–2025), glycerol, 1,2,4-butanetriol, sorbitol esters, 1,2,-6-hexanetriol, ethanol, isopropanol, butanediol, and mixtures thereof. Preferably, these solutions contain from about 0.01% to about 50% of the active compound, more preferably from about 0.1% to about 20%; and from about 1% to about 80% of an acceptable aqueous or organic solvent, more preferably from about 1% to about 40%.

If the topical pharmaceutical compositions of the present invention are formulated as an aerosol and applied to the skin as a spray-on, a propellant is added to a solution composition. A more complete disclosure of propellants useful herein can be found in Sagarin, Cosmetics Science and Technology, 2nd Edition, Vol. 2, pp. 443–465 (1972).

Topical pharmaceutical compositions of the present invention may be formulated as a solution comprising an emollient. An example of a composition formulated in this way would be a sunscreen-containing product. Preferably, such compositions contain from about 0.1% to about 50% of the active compound and from about 2% to about 50% of a topical pharmaceutically-acceptable emollient.

As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32–43 (1972), incorporated herein by reference, contains numerous examples of suitable materials.

A lotion can be made from a solution carrier system. Lotions preferably comprise from about 0.1% to about 20%, more preferably from about 1% to about 5%, of the active compound; from about 1% to about 20%, preferably from about 5% to about 10%, of an emollient; and from about 50% to about 90%, preferably from about 60% to about 80%, water.

Another type of product that may be formulated from a solution carrier system is a cream. A cream of the present invention would preferably comprise from about 0.1% to about 20%, more preferably from about 1% to about 5%, of the active compound; from about 5% to about 50%, preferably from about 10% to about 20%, of an emollient, and from about 45% to about 85%, preferably from about 50% to about 75%, water.

Yet another type of product that may be formulated from a solution carrier system is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may also comprise from about 2% to about 10% of an emollient plus from about 0.1% to about 2% of a thickening agent. A more complete disclosure of thickening agents useful herein can be found in Segarin, Cosmetics, Science and Technology, 2nd Edition, Vol. 1, pp. 72–73 (1972).

If the carrier is formulated as an emulsion, from about 1% to about 10%, preferably from about 2% to about 5%, of the carrier system comprises an emulsifier. Emulsifiers may be nonionic, anionic or cationic. Suitable emulsifiers are disclosed in, for example, U.S. Pat. No. 3,755,560, issued Aug. 28, 1973, Dickert et al; U.S. Pat. No. 4,421,769, issued Dec. 20, 1983, Dixon et al.; and McCutcheon's Detergents and Emulsifiers, North American Edition, pages 317–324 (1986); the disclosures of which are incorporated herein by reference. Preferred emulsifiers are anionic or nonionic, although the other types may also be used.

Lotions and creams can be formulated as emulsions as well as solutions. Preferably such lotions comprise from about 0.1% to about 20%, more preferably from about 1% to about 5%, of the active compound; from about 1% to about 20%, preferably from about 5% to about 10%, of an emollient; from about 25% to about 75%, preferably from about 45% to about 95%, water; and from about 0.1% to about 10%, preferably from about 0.5% to about 5%, of an emulsifier. Such creams would preferably comprise from about 0.1% to about 20%, more preferably from about 1% to about 5%, of the active compound; from about 1% to about 20%, preferably from about 5% to about 10%, of an emollient; from about 20% to about 80%, preferably from about 30% to about 70%, water; and from about 1% to about 10%, preferably from about 2% to about 5%, of an emulsifier.

Single emulsion skin care preparations, such as lotions and creams, of the oil-in-water type and water-in-oil type are well-known in the cosmetic art and are useful in the present invention. Multiphase emulsion compositions, such as the water-in-oil-in-water type, as disclosed in U.S. Pat. No. 4,254,105, Fakuda et al., issued Mar. 3, 1981, incorporated herein by reference, are also useful in the present invention. In general, such single or multiphase emulsions contain water, emollients and emulsifiers as essential ingredients.

Triple emulsion carrier systems comprising an oil-in-water-in-silicone fluid emulsion composition as disclosed in U.S. Pat. No. 4,960,764, Figueroa, issued Oct. 2, 1990, are also useful in the present invention. Preferably, this triple emulsion carrier system can be combined with from about 0.1% to about 20%, more preferably from about 1% to about 5%, of the active compound to yield the topical pharmaceutical composition of the present invention.

Another emulsion carrier system useful in the topical pharmaceutical compositions of the present invention is a micro-emulsion carrier system. Such a system comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name Tweens) or other nonionics; and from about 7% to about 20% water. This carrier system is preferably combined with from about 1% to about 5% of the active compound.

If the topical pharmaceutical compositions of the present invention are formulated as a gel or a cosmetic stick, a suitable amount of a thickening agent, as disclosed supra, is added to a cream or lotion formulation.

The topical pharmaceutical compositions of the present invention may also be formulated as makeup products such as foundations.

The topical pharmaceutical compositions of the present invention may also be formulated as medicated pads. Suitable examples of these pads are fully disclosed in U.S. Pat. Nos. 4,891,227 and 4,891,228, to Thaman et al., both issued Jan. 2, 1990 the disclosures of which are incorporated herein.

The topical pharmaceutical compositions of the present invention may contain, in addition to the aforementioned components, a wide variety of additional oil-soluble materials and/or water-soluble materials conventionally used in topical compositions, at their art-established levels.

Various water-soluble materials may also be present in the compositions of this invention. These include humectants, proteins and polypeptides, preservatives and an alkaline agent. In addition, the topical compositions herein can contain conventional cosmetic adjuvants, such as dyes, opacifiers (e.g., titanium dioxide), pigments and perfumes.

The topical pharmaceutical compositions of the present invention may also include a safe and effective amount of a penetration enhancing agent. A preferred amount of penetration enhancing agent is from about 1% to about 5% of the composition. Another useful penetration enhancer for the present invention is the non-ionic polymer under the CTFA designation: polyacrylamide and isoparrafin and laureth-7, available as Sepigel from Seppic Corporation. Also useful is polyquaternium-32 and mineral oil known as SalCare SC92 available from Allied Colloids, Suffolk, Va. This is a class of cationic polymers which are generally described in U.S. Pat. No. 4,628,078 to Glover et al. issued Dec. 9, 1986 and U.S. Pat. No. 4,599,379 to Flesher et al. issued Jul. 8, 1986 both of which are incorporated by reference herein.

Examples of useful penetration enhancers, among others, are disclosed in U.S. Pat. No. 4,537,776, Cooper, issued Aug. 27, 1985; U.S. Pat. No. 4,552,872, Cooper et al., issued Nov. 12, 1985; U.S. Pat. No. 4,557,934, Cooper, issued Dec. 10, 1985; U.S. Pat. No. 4,130,667, Smith, issued Dec. 19, 1978; U.S. Pat. No. 3,989,816, Rhaadhyaksha, issued Nov. 2, 1976; U.S. Pat. No. 4,017,641, DiGiulio, issued Apr. 12, 1977; and European Patent Application 0043738, Cooper et al., published Jan. 13, 1982.

Other conventional skin care product additives may also be included in the compositions of the present invention. For example, collagen, hyaluronic acid, elastin, hydrolysates, primrose oil, jojoba oil, epidermal growth factor, soybean saponins, mucopolysaccharides, and mixtures thereof may be used.

Various vitamins may also be included in the compositions of the present invention. For example, Vitamin A, ascorbic acid, Vitamin B, biotin, panthothenic acid, Vitamin D, Vitamin E and mixtures thereof and derivatives thereof are contemplated.

Also contemplated are skin cleaning compositions comprising both active compounds of the present invention and a cosmetically-acceptable surfactant. The term "cosmetically-acceptable surfactant" refers to a surfactant which is not only an effective skin cleanser, but also can be used without undue toxicity, irritation, allergic response, and the like. Furthermore, the surfactant must be capable of being commingled with the active compound in a manner such that there is no interaction which would substantially reduce the efficacy of the composition for regulating skin damage, e.g., wrinkles.

The skin cleaning compositions of the present invention preferably contain from about 0.1% to about 20%, preferably from about 1% to about 5%, of the creatine compound (e.g., creatine, cyclocreatine or another creatine compound) and from about 1% to about 90%, more preferably from about 1% to about 10%, of a cosmetically-acceptable surfactant.

The physical form of the skin cleansing compositions is not critical. The compositions can be, for example, formulated as toilet bars, liquids, pastes, mousses, or pads.

The surfactant component of the compositions of the present invention are selected from anionic, nonionic, zwitterionic, amphoteric and ampholytic surfactants, as well as mixtures of these surfactants. Such surfactants are well-known to those skilled in the detergency art.

The cleaning compositions of the present invention can optionally contain, at their art-established levels, materials which are conventionally used in skin cleansing compositions.

Sunblocks and sunscreens incorporating creatine compounds are also contemplated. The term "sun block" or "sun screen" includes compositions which block UV light. Examples of sunblocks include, for example, zinc oxide and titanium dioxide.

Sun radiation is one cause major cause of skin damage, e.g., wrinkles. Thus, for purposes of wrinkle treatment or prevention, the combination of creatine compounds with a UVA and/or UVB sunscreen would be advantageous. The inclusion of sunscreens in compositions of the present invention will provide immediate protection against acute UV damage. Thus, the sunscreen will prevent further skin damage caused by UV radiation, while the compounds of the invention regulates existing skin damage.

A wide variety of conventional sunscreening agents are suitable for use in combination with the active compound. Segarin, et al., at Chapter VIII, pages 189 et seq., of Cosmetics Science and Technology, disclose numerous suitable agents. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropyleneglycol esters); cinnamic acid derivatives (methyl and benzyl esters, .alpha.-phenyl cinnamonitrile; butyl cinnamoyl pyruvate); Dihydroxycinnamic acid derivatives (umbelliferone, methylumbelliferone, methylaceto-umbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxy-biphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbotol) (6-propyl piperonyl) ether; Hydroquinone; Benzophenones (Oxybenzene, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Iso-propyldibenzoylmethane; Butylmethoxydibenzoylmethane; Etocrylene; and 4-isopropyl-di-benzoylmethane.

Preferred sunscreens useful in the compositions of the present invention are 2-ethylhexyl-p-methoxycinnamate, butylmethoxydibenzoylmethane, 2-hydroxy-4-methoxybenzophenone, octyldimethyl-p-aminobenzoic acid and mixtures thereof.

A safe and effective amount of sunscreen may be used in the compositions of the present invention. The sunscreening agent must be compatible with the active compound. Generally the composition may comprise from about 1% to about 20%, preferably from about 2% to about 10%, of a sunscreening agent. Exact amounts will vary depending upon the sunscreen chosen and the desired Sun Protection Factor (SPF).

Also particularly useful in the present invention are sunscreens such as those disclosed in Sabatelli, U.S. patent application Ser. No. 054,085 (filed Jun. 2, 1987) and Sabatelli et al., U.S. patent application Ser. No 054,046 (filed Jun. 2, 1987). The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

An agent may also be added to any of the compositions of the present invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

In another embodiment of the present invention, an anti-inflammatory agent is included as an active agent along with the creatine compounds of the invention. The anti-inflammatory agent protects strongly in the UVA radiation range (though it also provides some UVB protection as well) thereby preventing further skin damage caused by UV radiation, while the creatine compounds of the invention treats existing damage. Thus the combination provides broad protection. The topical use of anti-inflammatory agents reduces photo-aging of the skin resulting from chronic exposure to UV radiation. (See U.S. Pat. No. 4,847,071, Bissett, Bush, and Chatterjee, issued Jul. 11, 1989, incorporated herein by reference; and U.S. Pat. No. 4,847,069, Bissett and Chatterjee, issued Jul. 11, 1989, incorporated herein by reference.)

A safe and effective amount of an anti-inflammatory agent may be added to the compositions of the present invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflupredinate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used.

A second class of anti-inflammatory agents which is useful in the compositions of the present invention includes the nonsteroidal anti-inflammatory agents. The variety of compounds encompassed by this group are well-known to those skilled in the art. For detailed disclosure of the chemical structure, synthesis, side effects, etc., of non-steroidal anti-inflammatory agents, reference may be had to standard texts, including Antiinflammatory and Anti-Rheumatic Drugs, K. D. Rainsford, Vol. I–III, CRC Press, Boca Raton, (1985), and Anti-inflammatory Agents. Chemistry and Pharmacology, 1, R. A. Scherrer, et al., Academic Press, New York (1974). Mixtures of these non-steroidal anti-inflammatory agents may also be employed, as well as the pharmaceutically-acceptable salts and esters of these agents. For example, etofenamate, a flufenamic acid derivative, is particularly useful for topical application. Yet another class of anti-inflammatory agents which are useful in the present invention are those disclosed in U.S. Pat. No. 4,912,248, Maeller, issued Mar. 27, 1990. This patent discloses compounds and diastereomeric mixtures of specific 2-naphthyl-containing ester compounds, especially naproxen ester and naproxol ester compounds, having two or more chiral centers. Finally, so-called "natural" anti-inflammatory agents are useful in the present invention. For example, candelilla wax, alpha bisabolol, aloe vera, Manjistha (extracted from plants in the genus *Rubia*, particularly *Rubia Cordifolia*), and Guggal (extracted from plants in the genus *Commiphora*, particularly *Commiphora Mukul*), may be used.

In another embodiment, the skin composition further comprises a safe and effective amount of a skin protectant. The skin protectant preferably comprises from about 0.001% to about 2%, more preferably from about 0.01% to about 1% of the composition. Useful skin protectants are disclosed in the Federal Register Vol. 48, No. 32 and include allantoin, aluminum hydroxide gel, bismuth subnitrate, boric acid, calamine, cocoa butter, corn starch, dimethicone, glycerin, kaolin, live yeast cell derivative, petrolatum, shark liver oil, sodium bicarbonate, sulfur, tannic acid, white petrolatum, zinc acetate, zinc carbonate and zinc oxide and mixtures thereof.

As set out above, certain embodiments of the present compounds can contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1–19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyls can be converted into esters via treatment with an esterifying agent such as alkanoyl halides. The term is further intended to include lower hydrocarbon groups capable of being solvated under physiological conditions, e.g., alkyl esters, methyl, ethyl and propyl esters. (See, for example, Berge et al., supra.)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the present invention include those suitable for topical, oral, nasal, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

The preparations of the present invention may be given parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Topical administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated effects, will range from about 0.0001 to about 1000 mg per kilogram of body weight per day. Creatine has been taken by athletes in the range of 2–30 gms per day with reasonable safety profile. Topical creams with 0.01–10% creatine are anticipated to be well tolerated. If desired, the effective daily dose of the active compound may be administered as two, three, four, five, six or more sub-doses administered separately at appropriate intervals throughout the day, optionally, in unit dosage forms.

The term "chronic treatment" includes continued treatment with a creatine compound over an extended period during a subject's lifetime, preferably for at least about three weeks, more preferably from about three months to about twenty years, more preferably from about six months to about ten years, more preferably still from about one year to about five years.

While it is possible for a compound of the present invention to be administered alone, it is preferable to administer the compound as a pharmaceutical composition.

In a further embodiment, the skin disorder is associated with free radicals, aging, sun radiation, stress or fatigue. In another embodiment, the subject is afflicted with wrinkles or is at risk for a skin disorder.

The term "associated with free radicals" includes any disorders or damaged to the skin resulting from, directly or indirectly from free radicals. The free radicals may be initiated by, for example, sun radiation (e.g., UV radiation) or pollution.

The term "aging" includes processes where there is oxidative damage, energy depletion or mitochondrial dysfunction where onset, amelioration, arrest, or elimination is effectuated by the creatine compounds described herein. Symptoms of aging include, but are not limited to, wrinkles, loss of elasticity of the skin and uneven pigmentation of the skin.

The term "subject" includes living organisms susceptible to skin damage or aging. Examples of subjects include humans, dogs, cats, horses, goats, cows, cattle. The term "subject" further is intended to include transgenic species.

The invention also features a composition for the treatment of the skin of a subject. The composition comprises an effective amount of creatine, creatine phosphate, a creatine compound or a salt thereof, and a pharmaceutically acceptable carrier. Preferably, the effective amount is effective to treat or prevent a skin disorder. Preferably, the composition is suitable for topical administration. The composition may be formulated as a lotion, cream, or ointment, gel or solid. In one advantageous embodiment, the composition also contains a sunblock or sunscreen (e.g., zinc oxide or titanium dioxide). In another further embodiment, the composition may be formulated as a cosmetic foundation or as a skin cleansing agent. Advantageously, the composition may contain a penetration agent. Examples of compounds which may be incorporated into the composition of the invention include, but are not limited to, hydroxyacids, retinols, Aloe, Chamomile, or mixtures thereof. In a further embodiment, the skin disorder is associated with free-radicals, aging, sun radiation, stress or fatigue.

In a further embodiment, the invention contemplates co-administering to the subject an effective amount of a skin preserving agent. Examples of skin preserving agents include antioxidants, such as ascorbic acid, vitamins, coenzyme Q10 (CoQ10) and its derivatives, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like. Preferred anti-oxidants include, CoQ10 and vitamin E. Other examples of skin preserving agents include energy-enhancing agents (e.g., ATP, nicotinamide or pyruvate), vitamins (e.g., E, C, B5, B6, and B9) and vitamin precursors.

The term "energy enhancing agents" also includes stimulants of mitochondrial function or ATP production elsewhere in the cell. Examples include intermediates such as, for example, pyruvate, nicotinamide and CoQ10.

Aging Oxidative Stress and Mitochondrial Dysfunction:

A common feature of the life cycle of virtually all multicellular organisms is the progressive decline in efficiency of various physiological processes once the productive phase of life is over. Data has supported the hypothesis that senescence cell death secondary to loss of functional capacity is due to accumulation of molecular oxidative damage (Harman 1956; Stadtman 1992; Ames et. al., 1993; Sohal 1995). The hypothesis is based on the fact that oxygen is potentially a toxic substance, and its use by aerobes, although necessary for their immediate survival, also may be hazardous to their long term existence. Molecular oxygen is the precursor of superoxide, hydrogen peroxide and hydroxyl radicals. Upon further reactions these could generate reactive oxygen species that cause extensive oxidative damage to macromolecules. Lipid peroxidation, DNA damage and carbonylation of proteins are some of the devastating effects. During aging there is an increase in the amount of oxidative stress which could be a result of increase in the rate of generation of reactive oxygen species, or the decline in anti-oxidative defenses or the decline in the efficiency of repair or removal of damaged molecules (Sohal et. al., 1996). With aging there is an increase in the production of ROS from mitochondria which results in damage to the inner mitochondrial membrane. By positive feedback mechanisms this results in further increase in ROS. Among flies, those with a longer life expectancy were shown to exhibit a lower rate of mitochondrial superoxide, hydrogen peroxide generation, a lower rate of protein oxidative damage, less DNA oxidative damage, higher activities of SOD and catalase, increased glutathione a versatile intracellular reductant. Variations in maximum life span among different species are often associated with differences in the metabolic rate (rate of oxygen consumption), metabolic potential (total amount of energy consumed per gram of body weight during life span) and level of oxidative stress. The highest degree of oxidative damage occur in tissues such as brain, heart and skeletal muscle which are composed primarily of long lived postmitotic cells. These tissues are also the targets of several age related degenerative disorders in which oxidative stress has been implicated (Davies 1995; Weindruch et al., 1993). Agents that minimize the production of reactive oxygen species are predicted to be protective.

Creatine Kinase Isoenzymes

Cells require energy to survive and to carry out the multitude of tasks that characterize biological activity. Cellular energy demand and supply are generally balanced and tightly regulated for economy and efficiency of energy. Creatine kinase plays a key role in the energy metabolism of cells with intermittently high and fluctuating energy requirements such as skeletal and cardiac muscle, brain and neural tissues, including, for example, the retina, spermatozoa and electrocytes use (Bessman 1985, Wallimann 1992, Wyss and Kaddurah-Daouk 1999). As stated above, the enzyme catalyzes the reversible transfer of the phosphoryl group from creatine phosphate to ADP, to generate ATP. There are multi-isoforms of creatine kinase (CK) which include muscle (CK-MM), brain (CK-BB) and mitochondrial (CK-Mia, CK-Mib) isoforms. The mitochondrial creatine kinases are located mainly between the inner and outer mitochondrial membranes where in association with the adenine nucleotide translocase and other proteins can transform ATP to phosphocreatine and transport it to other sites in the cell for energy utilization. The mitochondrial octameric creatine kinase has been implicated in mitochondrial permeability transition and cell death processes (O'Gorman 1997). Creatine is an excellent stimulant of oxidative phosphorylation and seems to induce octameric mitochondrial creatine kinase formation and inhibits mitochondrial pore opening. The cytoplasmic isoforms utilize phosphocreatine to produce ATP for cell work. A communication between the mitochondrial and cytoplasmic isoforms through the substrates creatine and phosphocreatine ensures connectivity between sites of energy production and sites of energy consumption.

Experimental data suggest that CK is located near the sites in cells where energy generation occurs; e.g., where force generation by motor proteins takes place, next to ion pumps and transporters in membranes and where other ATP-dependent processes take place. It seems to play a complex multi-faceted role in cellular energy homeostasis. The creatine kinase system is involved in energy buffering/ energy transport activities. It also is involved in regulating ADP and ATP levels intracellularly as well as ADP/ATP ratios. Proton buffering and production of inorganic phosphate are important parts of the system.

Creatine Kinase Skin Aging and Skin Damage

The creatine content and the efficiency of the creatine kinase system decreases with aging. Aging and several insults result in oxidative stress state and energy compromise. It is demonstrate here that modulation of the creatine kinase system results in minimizing the rate of production of molecules associated with oxidative damage. Such minimization combined with energy boosting effects should slow damage to tissue during aging or exposure to insults. Creatine and analogs of creatine that modify the rate of ATP synthesis through creatine kinase could sustain energy production, mitochondrial function, and protect against free radical production. Such effects could have positive impact against aging or insult related skin damage.

The components of the creatine kinase/phosphocreatine system include the enzyme creatine kinase, the substrates creatine and creatine phosphate, and the transporter of creatine. Some of the functions associated with this system include efficient regeneration of energy in cells with fluctuating and high energy demand, phosphoryl transfer activity, ion transport regulation, cytoskeletal association, nucle otide pool preservation, proton buffering, and involvement in signal transduction pathways.

Without wishing to be bound by theory, it is thought that modulating the creatine kinase activity would modulate energy flow and affect skin cell function, integrity and survival. An activated energy state should minimizes oxidative damage and enable cells to withstand insult secondary to aging or insults such as UV radiation.

Creatine is taken by athletes to boost muscle function during burst activity (for review see Wyss and Kaddurah-Daouk 1999) and during competitions. Creatine was shown to have neuroprotective properties in several animal models of neurodegenerative diseases (Matthews et al., 1988; Kliveny et al 1999; Matthews et. al., 1999).

Ingestion of creatine analogs has been shown to result in replacement of tissue phosphocreatine pools by synthetic phosphagens with different kinetic and thermodynamic properties. This results in subtle changes of intracellular energy metabolism, including the increase of total reserves of high energy phosphate (see refs. Roberts, J. J. and J. B. Walker, *Arch Biochem. Biophys* 220(2): 563–571 (1983)). The replacement of phosphocreatine pools with slower acting synthetic phosphagens, such as creatine analogs might benefit neurological disorders by providing a longer lasting source of energy. One such analog, cyclocreatine (1-carboxymethyl-2-aminoimidazolidine) modifies the flow of energy of cells in stress and may interfere with ATP utilization at sites of cellular work.

Creatine Compounds Useful in Skin Care

Creatine compounds useful in the present invention include compounds which modulate one or more of the structural or functional components of the creatine kinase/phosphocreatine system. Compounds which are effective for this purpose include creatine, creatine phosphate and analogs thereof, compounds which mimic their activity, and salts of these compounds as defined above. Exemplary creatine compounds are described below.

Creatine (also known as N-(aminoiminomethyl)-N-methylglycine; methylglycosamine or N-methyl-guanido acetic acid) is a well-known substance. (See, *The Merck Index*, Eleventh Edition, No. 2570 (1989).

Creatine is phosphorylated chemically or enzymatically by creatine kinase to generate creatine phosphate, which also is well-known (see, *The Merck Index*, No. 7315). Both creatine and creatine phosphate (phosphocreatine) can be extracted from animal tissue or synthesized chemically. Both are commercially available.

Cyclocreatine is an essentially planar cyclic analog of creatine. Although cyclocreatine is structurally similar to creatine, the two compounds are distinguishable both kinetically and thermodynamically. Cyclocreatine is phosphorylated efficiently by creatine kinase in the forward reaction both in vitro and in vivo. Rowley, G. L., *J. Am. Chem. Soc.* 93: 5542–5551 (1971); McLaughlin, A. C. et. al., *J. Biol. Chem.* 247, 4382–4388 (1972).

The phosphorylated compound phosphocyclocreatine is structurally similar to phosphocreatine; however, the phosphorous-nitrogen (P—N) bond of cyclocreatine phosphate is more stable than that of phosphocreatine. LoPresti, P. and M. Cohn, *Biochem. Biophys. Acta* 998: 317–320 (1989); Annesley, T. M. and J. B. Walker, J. Biol. Chem. 253; 8120–8125, (1978); Annesley, T. M. and J. B. Walker, *Biochem. Biophys. Res. Commun.* 74:185–190 (1977).

3-Guanidinopropionic acid (3-GPA) is an endogenous metabolite found in animals and humans (Hiraga et. al., J. of Chromatography vol 342, 269–275, 1985; Watanabe et. al., Guanidines edited by Mori et. al., Plenum, N.Y., 49–58, 1983). The compound is available from Sigma chemicals and is an extensively studied analog of creatine.

Guanidino acetate is yet another analog of creatine and is a precursor of creatine in its biosynthetic pathway.

Guanidino benzoic acids are structurally related to creatine. Also compounds that attach amino acid like molecules covalently to creatine are creatine compounds of interest. Examples are creatine-ascorbate and creatine-pyruvate. Other types of molecules could be covalently attached.

Creatine analogs and other agents which act to interfere with the activity of creatine biosynthetic enzymes or with the creatine transporter are useful in the present method of treating or preventing age related damage. Thus the effects of such compounds can be direct or indirect, operating by mechanisms including, but not limited to, influencing the uptake or biosynthesis of creatine, the function of the creatine phosphate shuttle, enzyme activity, or the activity of associated enzymes, or altering the levels of substrates or products of a reaction to alter the velocity of the reaction.

Substances known or believed to modify energy production through the creatine kinase/phosphocreatine system which can be used in the present method are described below. Exemplary compounds are shown in Tables 1 and 2.

It will be possible to modify the substances described below to produce analogs which have enhanced characteristics, such as greater specificity for the enzyme, enhanced stability, enhanced uptake into cells, or better binding activity.

Compounds which modify the structure or function of the creatine kinase/creatine phosphate system directly or indirectly are useful in preventing and/or treating age related damage to tissue such as skin.

Molecules that regulate the transporter of creatine, or the association of creatine kinase with other protein or lipid molecules in the membrane, the substrates concentration creatine and creatine phosphate also are useful in preventing and/or treating age related damage to tissue such as skin.

Compounds which are useful in the present invention can be substrates, enzyme activity modifiers or substrate analogs of creatine kinase. In addition, modulators of the enzymes that work in conjunction with creatine kinase now can be designed and used, individually, in combination or in addition to creatine compounds. Combinations of creatine compounds with other supplements or other drugs is proposed.

The pathways of biosynthesis and metabolism of creatine and creatine phosphate can be targeted in selecting and designing compounds which may modify energy production or high energy phosphoryl transfer through the creatine kinase system. Compounds targeted to specific steps may rely on structural analogies with either creatine or its precursors. Novel creatine analogs differing from creatine by substitution, chain extension, and/or cyclization may be designed. The substrates of multisubstrate enzymes may be covalently linked, or analogs which mimic portions of the different substrates may be designed. Non-hydrolyzable phosphorylated analogs can also be designed to mimic creatine phosphate without sustaining ATP production.

A number of creatine and creatine phosphate analogs have been previously described in the literature or can be readily synthesized. Examples are these shown in Table 1 and Table 2. Some of them are slow substrates for creatine kinase.

Tables 1 and 2 illustrate the structures of creatine, cyclocreatine (1-carboxymethyl-2-iminoimidazolidine), N-phosphorocreatine (N-phosphoryl creatine), cyclocreatine phosphate (3-phosphoryl-1-carboxymethyl-2-iminoimidazolidine) and other

TABLE 1
CREATINE ANALOGS
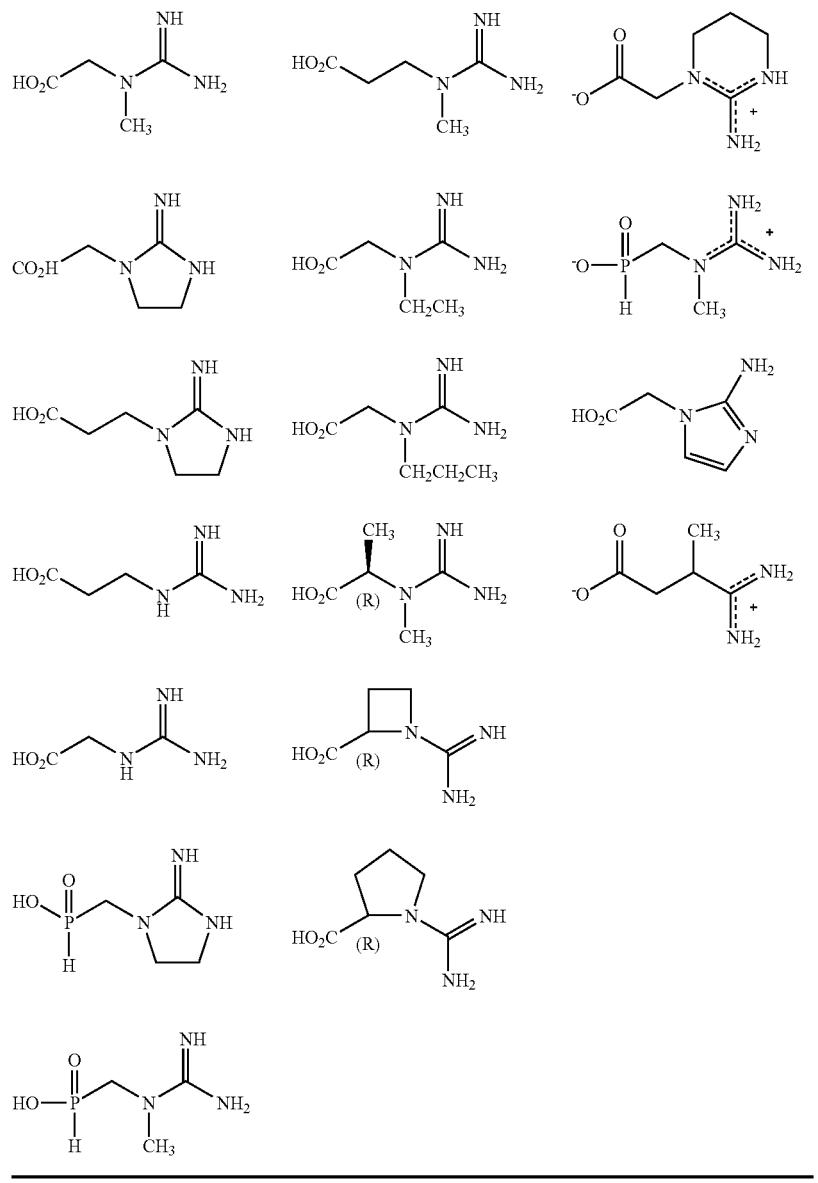
TABLE 2
CREATINE PHOSPHATE ANALOGS
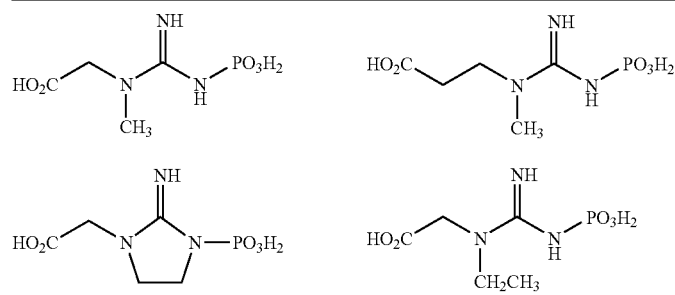

TABLE 2-continued

CREATINE PHOSPHATE ANALOGS

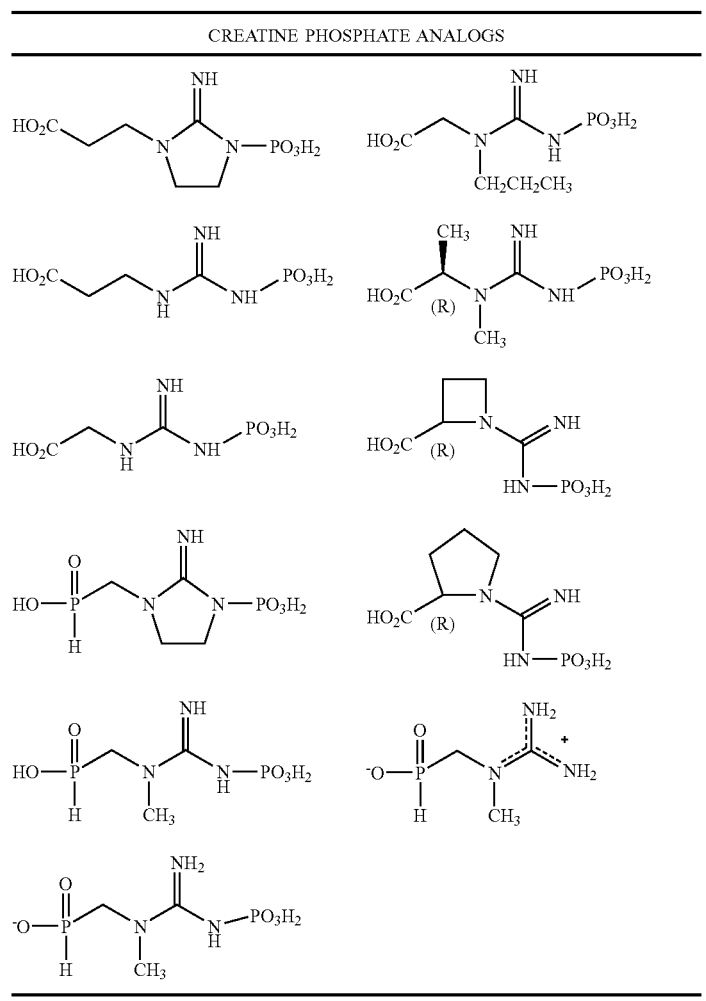

compounds. In addition, 1-carboxymethyl-2-aminoimidazole, 1-carboxymethyl-2 2-iminomethylimidazolidine, 1-carboxyethyl-2-iminoimidazolidine, N-ethyl-N-amidinoglycine and b-guanidinopropionic acid are believed to be effective.

Cyclocreatine (1-carboxymethyl-2-iminoimidazolidine) is an example of a class of substrate analogs of creatine kinase, which can be phosphorylated by creatine kinase and which are believed to be active.

A class of creatine kinase targeted compounds are bi-substrate analogs comprising an adenosine-like moiety linked via a modifiable bridge to a creatine link moiety (i.e., creatine or a creatine analog). Such compounds are expected to bind with greater affinity than the sum of the binding interaction of each individual substrate (e.g., creatine and ATP). The modifiable bridge linking an adenosine-like moiety at the 5'-carbon to a creatine like moiety can be a carbonyl group, alkyl (a branched or straight chain hydrocarbon group having one or more carbon atoms), or substituted alkyl group (an alkyl group bearing one or more functionalities, including but not limited to unsaturation, heteroatom-substituents, carboxylic and inorganic acid derivatives, and electrophilic moieties). Also the linking of creatine to other molecules that are energy enhancing or vitamins or antioxidants is recommended. Examples are creatine-pyruvate or creatine-ascorbate.

N-phosphorocreatine analogs also can be designed which bear non-transferable moieties which mimic the N-phosphoryl group. These cannot sustain ATP production.

In one embodiment, the invention features methods of treating skin disorders by administering to a subject an effective amount of a creatine compound represented by the general formula I:

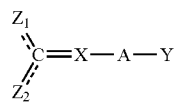

and pharmaceutically acceptable salts thereof, wherein:

a) Y is selected from the group consisting of: —$CO_2H$—NHOH, —$NO_2$, —$SO_3H$, —C(=O)NH$SO_2$J and —P(=O)(OH)(OJ), wherein J is selected from the group consisting of: hydrogen, $C_1$–$C_6$ straight chain alkyl, $C_3$–$C_6$ branched alkyl, $C_2$–$C_6$ alkenyl, $C_3$–$C_6$ branched alkenyl, and aryl;

b) A is selected from the group consisting of: C, CH, $C_1$–$C_5$alkyl, $C_2$–$C_5$alkenyl, $C_2$–$C_5$alkynyl, and $C_1$–$C_5$alkoyl chain, each having 0–2 substituents which are selected independently from the group consisting of:
  1) K, where K is selected from the group consisting of: $C_1$–$C_6$ straight alkyl, $C_2$–$C_6$ straight alkenyl, $C_1$–$C_6$ straight alkoyl, $C_3$–$C_6$ branched alkyl, $C_3$–$C_6$ branched alkenyl, and $C_4$–$C_6$ branched alkoyl, K having 0–2 substituents independently selected from the group consisting of: bromo, chloro, epoxy and acetoxy;
  2) an aryl group selected from the group consisting of: a 1–2 ring carbocycle and a 1–2 ring heterocycle, wherein the aryl group contains 0–2 substituents independently selected from the group consisting of: —$CH_2L$ and —$COCH_2L$ where L is independently selected from the group consisting of: bromo, chloro, epoxy and acetoxy; and
  3) —NH-M, wherein M is selected from the group consisting of: hydrogen, $C_1$–$C_4$ alkyl, $C_2$–$C_4$ alkenyl, $C_1$–$C_4$ alkoyl, $C_3$–$C_4$ branched alkyl, $C_3$–$C_4$ branched alkenyl, and $C_4$ branched alkoyl;
c) X is selected from the group consisting of $NR_1$, $CHR_1$, $CR_1$, O and S, wherein $R_1$ is selected from the group consisting of:
  1) hydrogen;
  2) K where K is selected from the group consisting of: $C_1$–$C_6$ straight alkyl, $C_2$–$C_6$ straight alkenyl, $C_1$–$C_6$ straight alkoyl, $C_3$–$C_6$ branched alkyl, $C_3$–$C_6$ branched alkenyl, and $C_4$–$C_6$ branched alkoyl, K having 0–2 substituents independently selected from the group consisting of: bromo, chloro, epoxy and acetoxy;
  3) an aryl group selected from the group consisting of a 1–2 ring carbocycle and a 1–2 ring heterocycle, wherein the aryl group contains 0–2 substituents independently selected from the group consisting of: —$CH_2L$ and —$COCH_2L$ where L is independently selected from the group consisting of: bromo, chloro, epoxy and acetoxy;
  4) a $C_5$–$C_9$ a-amino-w-methyl-w-adenosylcarboxylic acid attached via the w-methyl carbon;
  5) 2 $C_5$–$C_9$ a-amino-w-aza-w-methyl-w-adenosylcarboxylic acid attached via the w-methyl carbon; and
  6) a $C_5$–$C_9$ a-amino-w-thia-w-methyl-w-adenosylcarboxylic acid attached via the w-methyl carbon;
d) $Z_1$ and $Z_2$ are chosen independently from the group consisting of: =O, —$NHR_2$, —$CH_2R_2$, —$NR_2OH$; wherein $Z_1$ and $Z_2$ may not both be =O and wherein $R_2$ is selected from the group consisting of:
  1) hydrogen;
  2) K, where K is selected from the group consisting of: $C_1$–$C_6$ straight alkyl; $C_2$–$C_6$ straight alkenyl, $C_1$–$C_6$ straight alkoyl, $C_3$–$C_6$ branched alkyl, $C_3$–$C_6$ branched alkenyl, and $C_4$–$C_6$ branched alkoyl, K having 0–2 substituents independently selected from the group consisting of: bromo, chloro, epoxy and acetoxy;
  3) an aryl group selected from the group consisting of a 1–2 ring carbocycle and a 1–2 ring heterocycle, wherein the aryl group contains 0–2 substituents independently selected from the group consisting of: —$CH_2L$ and —$COCH_2L$ where L is independently selected from the group consisting of: bromo, chloro, epoxy and acetoxy;
  4) 2 $C_4$–$C_8$ a-amino-carboxylic acid attached via the w-carbon;
  5) B, wherein B is selected from the group consisting of: —$CO_2H$—NHOH, —$SO_3H$, —$NO_2$, OP(=O)(OH)(OJ) and —P(=O)(OH)(OJ), wherein J is selected from the group consisting of: hydrogen, $C_1$–$C_6$ straight alkyl, $C_3$–$C_6$ branched alkyl, $C_2$–$C_6$ alkenyl, $C_3$–$C_6$ branched alkenyl, and aryl, wherein B is optionally connected to the nitrogen via a linker selected from the group consisting of: $C_1$–$C_2$ alkyl, $C_2$ alkenyl, and $C_1$–$C_2$ alkoyl;
  6) -D-E, wherein D is selected from the group consisting of: $C_1$–$C_3$ straight alkyl, $C_3$ branched alkyl, $C_2$–$C_3$ straight alkenyl, $C_3$ branched alkenyl, $C_1$–$C_3$ straight alkoyl, aryl and aroyl; and E is selected from the group consisting of: —$(PO_3)_n$NMP, where n is 0–2 and NMP is ribonucleotide monophosphate connected via the 5'-phosphate, 3'-phosphate or the aromatic ring of the base; —$[P(=O)(OCH_3)(O)]_m$-Q, where m is 0–3 and Q is a ribonucleoside connected via the ribose or the aromatic ring of the base; —$[P(=O)(OH)(CH_2)]_m$-Q, where m is 0–3 and Q is a ribonucleoside connected via the ribose or the aromatic ring of the base; and an aryl group containing 0–3 substituents chosen independently from the group consisting of: Cl, Br, epoxy, acetoxy, —OG, —C(=O)G, and —$CO_2G$, where G is independently selected from the group consisting of: $C_1$–$C_6$ straight alkyl, $C_2$–$C_6$ straight alkenyl, $C_1$–$C_6$ straight alkoyl, $C_3$–$C_6$ branched alkyl, $C_3$–$C_6$ branched alkenyl, $C_4$–$C_6$ branched alkoyl, wherein E may be attached to any point to D, and if D is alkyl or alkenyl, D may be connected at either or both ends by an amide linkage; and
  7) -E, wherein E is selected from the group consisting of —$(PO_3)_n$NMP, where n is 0–2 and NMP is a ribonucleotide monophosphate connected via the 5'-phosphate, 3'-phosphate or the aromatic ring of the base; —$[P(=O)(OCH_3)(O)]_m$-Q, where m is 0–3 and Q is a ribonucleoside connected via the ribose or the aromatic ring of the base; —$[P(=O)(OH)(CH_2)]_m$-Q, where m is 0–3 and Q is a ribonucleoside connected via the ribose or the aromatic ring of the base; and an aryl group containing 0–3 substituents chose independently from the group consisting of: Cl, Br, epoxy, acetoxy, —OG, —C(=O)G, and —$CO_2G$, where G is independently selected from the group consisting of: $C_1$–$C_6$ straight alkyl, $C_2$–$C_6$ straight alkenyl, $C_1$–$C_6$ straight alkoyl, $C_3$–$C_6$ branched alkyl, $C_3$–$C_6$ branched alkenyl, $C_4$–$C_6$ branched alkoyl; and if E is aryl, E may be connected by an amide linkage;
e) if $R_1$ and at least one $R_2$ group are present, $R_1$ may be connected by a single or double bond to an $R_2$ group to form a cycle of 5 to 7 members;
f) if two $R_2$ groups are present, they may be connected by a single or a double bond to form a cycle of 4 to 7 members; and
g) if $R_1$ is present and $Z_1$ or $Z_2$ is selected from the group consisting of —$NHR_2$, —$CH_2R_2$ and —$NR_2OH$, then $R_1$ may be connected by a single or double bond to the carbon or nitrogen of either $Z_1$ or $Z_2$ to form a cycle of 4 to 7 members.

Creatine, creatine phosphate and many creatine analogs are commercially available. Additionally, analogs of creatine may be synthesized using conventional techniques. For example, creatine can be used as the starting material for synthesizing at least some of the analogs encompassed by formula I. Appropriate synthesis reagents, e.g. alkylating, alkenylating or alkynylating agents may be used to attach the respective groups to target sites. Alternatively, reagents capable of inserting spacer groups may be used to alter the creatine structure. Sites other than the target site are protected using conventional protecting groups while the desired sites are being targeted by synthetic reagents.

If the creatine analog contains a ring structure, then the analog may be synthesized in a manner analogous to that described for cyclocreatine (Wang, T., *J. Org. Chem,* 39:3591–3594 (1974)). The various other substituent groups may be introduced before or after the ring is formed.

Many creatine analogs have been previously synthesized and described (Rowley et al., *J. Am. Chem. Soc.* 93:5542–5551 (1971); McLaughlin et al., *J. Biol. Chem.* 247:4382–4388 (1972); Nguyen, A.C.K., "Synthesis and enzyme studies using creatine analogs", Thesis, Dept. of Pharmaceutical Chemistry, Univ. Calif., San Francisco (1983); Lowe et al., *J. Biol. Chem.* 225:3944–3951 (1980); Roberts et al., *J. Biol. Chem.* 260:13502–13508 (1985); Roberts et al., *Arch. Biochem. Biophys.* 220:563–571 (1983), and Griffiths et al., *J. Biol. Chem.* 251:2049–2054 (1976)). The contents of all of the aforementioned references are expressly incorporated by reference. Further to the aforementioned references, Kaddurah-Daouk et al. (WO92/08456; WO90/09192; U.S. Pat. No. 5,324,731; U.S. Pat. No. 5,321,030) also provide citations for the synthesis of a plurality of creatine analogs. Also the synthesis of creatine-pyruvate and creatine ascorbate has been described in a series of patents WPI 98-481123/199841; WPI 98-457997/199840; WPI 98-387651/199833). The contents of all the aforementioned references and patents are incorporated herein by reference.

Creatine compounds which currently are available or have been synthesized include, for example, creatine, b-guanidinopropionic acid, guanidinoacetic acid, creatine phosphate disodium salt, cyclocreatine, homocyclocreatine, phosphinic creatine, homocreatine, ethylcreatine, cyclocreatine phosphate dilithium salt and guanidinoacetic acid phosphate disodium salt, 4 guanidino benzoic acid and derivatives, creatine-pyruvate, creatine-ascorbate among others.

Creatine phosphate compounds also can be synthesized chemically or enzymatically. The chemical synthesis is well known. Annesley, T. M. Walker, J. B., *Biochem. Biophys. Res. Commun.,* (1977), 74, 185–190; Cramer, F., Scheiffele, E., Vollmar, A., *Chem. Ber.,* (1962), 95, 1670–1682.

Salts of the products may be exchanged to other salts using standard protocols. The enzymatic synthesis utilizes the creatine kinase enzyme, which is commercially available, to phosphorylate the creatine compounds. ATP is required by creatine kinase for phosphorylation, hence it needs to be continuously replenished to drive the reaction forward. It is necessary to couple the creatine kinase reaction to another reaction that generates ATP to drive it forward. The purity of the resulting compounds can be confirmed using known analytical techniques including $^1$H NMR, $^{13}$CNMR Spectra, Thin layer chromatography, HPLC and elemental analysis.

Modes of Administration

The creatine compound can be administered to the afflicted individual alone or in combination with another creatine analog or other agent. The other agents could be approved therapies, supplements that protect against oxidative damage, energy enhancers, sugars, intermediates of metabolism and nutrients among others. The creatine compounds can be administered as pharmaceutically acceptable salts in a pharmaceutically acceptable carrier. The compound may be administered to the subject by a variety of routes, including, but not necessarily limited to topical, oral (dietary), transdermal, or parenteral (e.g., subcutaneous, intramuscular, intravenous injection, bolus or continuous infusion) routes of administration, for example. An effective amount (i.e., one that is sufficient to produce the desired effect in an individual) of a composition comprising a creatine analog is administered to the individual. The actual amount of drug to be administered will depend on factors such as the size and age of the individual, in addition to the severity of symptoms, other medical conditions and the desired aim of treatment. As discussed above, preferably the compound is administered topically.

Previous studies have described the administration and efficacy of creatine compounds in vivo. For example, creatine phosphate has been administered to patients with cardiac diseases by intravenous injection. Up to 8 grams/day were administered with no adverse side effects. Athletes and body builders take creatine monohydrate at 2–30 grams per day with an initial loading phase where 20 grams per day are used followed by 2–5 grams per day to sustain levels. The efficacy of selected creatine kinase substrate analogs to sustain ATP levels or delay rigor during ischemic episodes in muscle has been investigated. On one study, cyclocreatine was fed to mice, rats and chicks, and appeared to be well-tolerated in these animals. Newly hatched chicks were fed a diet containing 1% cyclocreatine. In the presence of antibiotics, the chicks tolerated 1% cyclocreatine without significant mortality, although the chicks grew more slowly than control chicks (Griffiths, G. R. and J. B. Walker, *J. Biol. Chem.* 251(7): 2049–2054 (1976)). In another study, mice were fed a diet containing 1% cyclocreatine for 10 days (Annesley, T. M. and J. B. Walker, *J. Biol. Chem.* 253(22): 8120–8125 (1978)). Cyclocreatine has been feed to mice at up to 1% of their diet for 2 weeks or for over 4 weeks without gross adverse effects. Lillie et al., *Cancer Res.,* 53: 3172–3178 (1993). Feeding animals cyclocreatine (e.g., 1% dietary) has been shown to lead to accumulation of cyclocreatine in different organs in mM concentrations. For example, cyclocreatine was reported to be taken up by muscle, heart and brain in rats receiving dietary 1% cyclocreatine. Griffiths, G. R. and J. B. Walker, *J. Biol. Chem.* 251(7): 2049–2054 (1976). As shown previously, antiviral activity of cyclocreatine is observed on administering 1% dietary cyclocreatine. Many of the above-referenced studies show that creatine analogs are been shown to be capable of crossing the blood-brain barrier. Creatine as 1%–3% of the diet was shown to have beneficial effects on Huntington's disease.

The creatine compound can be formulated according to the selected route of administration (e.g., emulsion, solution, cream, powder, tablet, capsule, transdermal patch, implantable capsule). An appropriate composition comprising a creatine analog can be prepared in a physiologically acceptable vehicle or carrier. For example, a composition in tablet form can include one or more additives such as a filler (e.g., lactose), a binder (e.g., gelatin, carboxymethylcellulose, gum arabic), a flavoring agent, a coloring agent, or coating material as desired. For solutions or emulsions in general, carriers may include aqueous or alcoholic/aqueous solutions, emulsions or suspensions, including saline and buffered media. Parenteral vehicles can include sodium chloride, solution, Ringer's dextrose, dextrose and sodium chloride, lactated Ringer's or fixed oils. In addition, intravenous vehicles can include fluid and nutrient replenishers, and electrolyte replenishers, such as those based on Ringer's dextrose. Preservatives and other additives can also be present. For example, antimicrobial, antioxidant, chelating agents, and inert gases can be added. (See, generally, Remington's Pharmaceutical Sciences, 16th Edition, Mack, Ed., 1980).

The term "administration" is intended to include routes of administration which allow the creatine compounds to perform their intended function(s) of preventing, ameliorating, arresting, and/or eliminating disease(s) of the nervous system in a subject. Examples of routes of administration which may be used include injection (topical, oral, subcutaneous, intravenous, parenterally, intraperitoneally, inhalation, transdermal, and rectal. Depending on the route of administration, the creatine-like compound may be coated with or in a material to protect it from the natural conditions which may detrimentally effect its ability to perform its intended function. The administration of the creatine-like compound is done at dosages and for periods of time effective to reduce, ameliorate or eliminate the symptoms of aging. Dosage regimes may be adjusted for purposes of improving the therapeutic or prophylactic response of the compound. For example, several divided doses may be administered daily or the dose may be proportionally reduced as indicated by the exigencies of the therapeutic situation.

EXEMPLIFICATION OF THE INVENTION

1. Effects of 1% Creatine Supplementation on 3-Nitrotyrosine/Tyrosine Concentration in FALS Mice.

Oxidative injury involves the activation of nitric oxide production, and peroxynitrite which results in nitration of proteins. The nitration of proteins could be determined by measuring the ratio of 3-nitrotryrosine to tyrosine. The FALS mice are transgenic animals that express a mutant form of Cu/Zn superoxide dismutase found in patients with familial ALS (Amyotrophic Lateral Sclerosis). These animals develop ALS symptoms with gradual motor neuron loss, muscle weakness, and die within 135 days. Oxidative stress has been associated with the death of motor neurons. Levels of 3-nitrotyrosine are significantly increased in the spinal cords of these mice (Ferrante 1997). The transgenic mice with the G93A mutation and the littermate controls (eight mice per group) were fed 1% creatine or unsupplemented diets at days 70 of age and then killed at 120 days of age for measurements of 3-nitrotyrosine as described (Ferrante 1997). FIG. 1 (left panel) demonstrates that creatine can significantly inhibit the higher levels of 3 nitrotyrosine/tyrosine levels in lower spinal cords of transgenic FALS. The right panel also demonstrates that creatine can inhibit the activation of production of 3-nitrotyrosine/tyrosine in the upper spinal cords.

2. Effect of 1% Creatine Supplementation on Hydroxyl Radical Production as Measured by Rate of Conversion of Salicylate to its by Products in FALS Mice.

Figure 2:
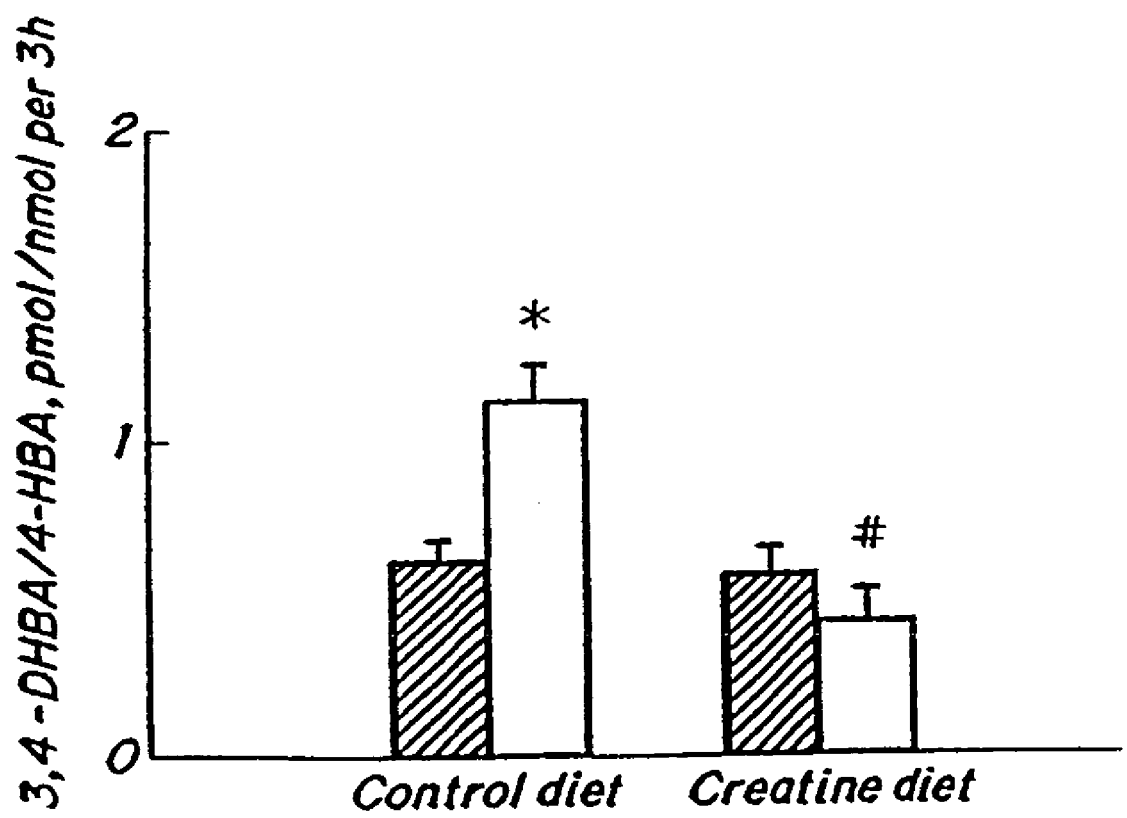
FIG. 2 depicts the effect of 1% creatine supplementation on hydroxyl radical production as measured by rate of conversion of salicylate to its by products in FALS mice (G93A transgenic mice) after systemic administration of mitochondrial toxin 3-NP. Administration of 3-NP resulted in a significant increase in the ratio of 3,4DHBA to 4HBA in mice fed normal diets, which was significantly attenuated in mice receiving 1% creatine supplementation. Black column represents basal levels, white after 3-NP administration. *p less than 0.05, compared with basal levels; # p less than 0.05 compared with mice treated with 3-NP and fed a control diet.

The level of free radical production in vivo can be determined using the microdialysis technique (Matthews et al 1998). Administration of the mitochondrial toxin 3-nitropropionic acid results in a significant increase in the conversion of salicylate to 2,3-DHBA in the striatum, which is blocked in mice over expressing Cu, Zn SOD (Bogdanov et. al., 1998). Here we demonstrate that systemic administration of 3-nitropropionic acid (3-NP) resulted in a significant increase in the conversion of 4-HBA to 3,4-DHBA in G93 A transgenic mice fed unsupplemented diets (FIG. 2). In animals fed 1% creatine supplemented diets, there was no significant increase in 3,4 DHBA/4HBA after 3-NP administration. This demonstrates that creatine can minimize the production of hydroxyl radicals that are implicated in aging related damage.

3. Production of 2,3 and 2,5 DHBA and 3 Nitrotyrosine (Indicators of Oxidative Stress) after Intrastriatal Injection of Malonate in Control Animals Fed with Creatine and Those Fed with Cyclocreatine The salicylate hydroxyl radical-trapping method was used for measuring levels of hydroxyl radicals in striatal tissue after malonate injections. Eight animals in each group were fed either a normal diet or a diet enriched with 1% creatine or 1% cyclocreatine for two weeks before intrastriatal malonate injections. Animals were injected with 200 mg/kg salicylate intraperitoneally just before the malonate injections and were killed 1 hour later. The striata were then dissected rapidly from a 2-mm thick slice and placed in 0.25 ml of chilled 0.1 M perchloric acid. Samples were subsequently sonicated, frozen rapidly and thawed and centrifuged twice. An aliquot of supernatant was analyzed by HPLC with the 16-electrode electrochemical detection (Beal et. al., 1990). Salicylate, 2,3 and 2,5 DHBA, tyrosine, 3-nitrotyrosine were measured electrochemically by oxidation at 840, 240, 120, 600 and 840 mV respectively with retention times of 20.5, 9.4, 6.3, 10.5, 18.2 min respectively. The data were expressed as the ratio of 2,3 and 2,5 DHBA to salicylate to normalize the DHBA concentrations for differing brain concentrations of salicylate. Similarly, 3-nitrotyrosine levels were normalized to tyrosine levels. We also examined the effects of 1% creatine supplementation for 2 weeks on 3-NP induced increases in 3-nitrotyrosine levels. Male Sprague Dawley rats were treated with 3-NP at a dose of 20 mg/kg intraperotoneally and then killed at 3 hours. Ten animals were examined in each group. The striata were dissected and placed in chilled 0.1 M perchloric acid. 3-Nitrotyrosine and tyrosine concentrations were measured by HPLC with electrochemical detection (Matthews 1998). Statistical comparisons were made by unpaired Student's t test or by one way ANOVA followed by Fisher's protected least significant difference test for post hoc comparisons.

Figure 3:
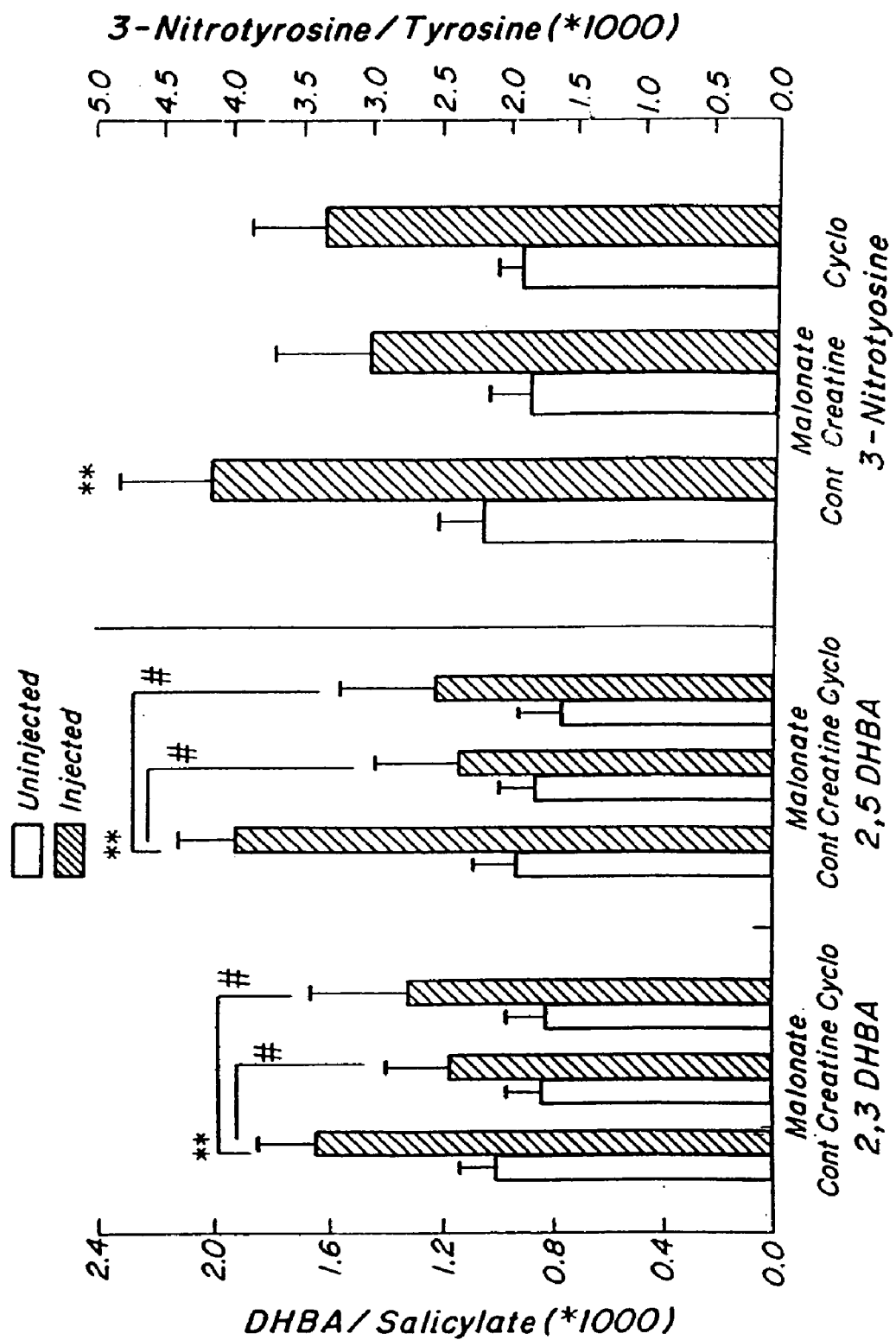
FIG. 3 depicts the production of 2,3 and 2,5 DHBA and 3 nitrotyrosine after intrastriatal injection of malonate in control animals fed with creatine and those fed with cyclocreatine. **p is less than 0.01 compared with uninjected side; #p is less than 0.05 compared with DHBA elevation in controls. Eight animals were used in each group.
Figure 4:
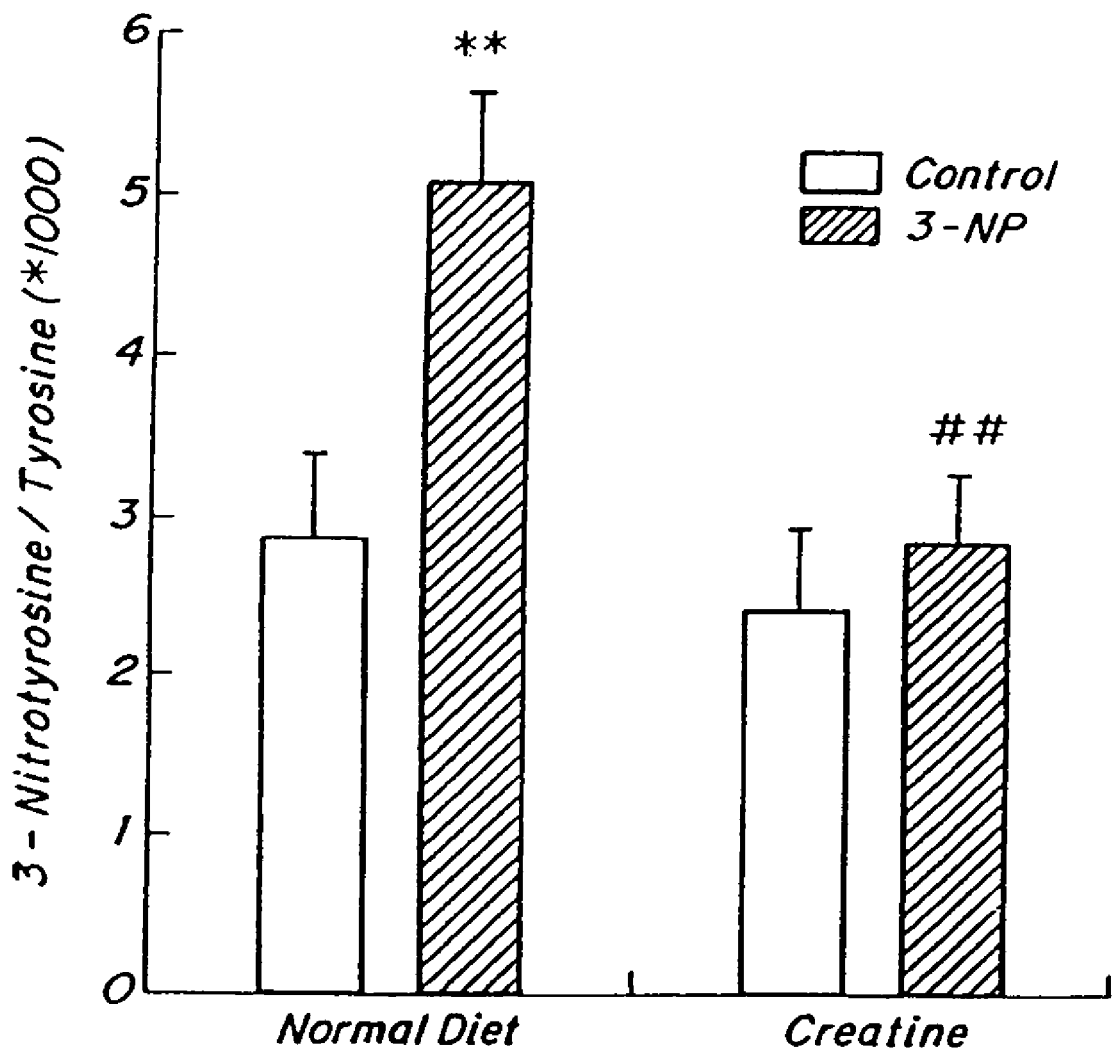
FIG. 4 depicts 3-Nitrotyrosine levels after systemic administration of the mitochondrial toxin 3-NP to controls and creatine-fed animals. **p is less than 0.01 compared with saline controls. ##p is less than 0.01 compared with 3-NP injected animals on a normal diet. Ten animals were used in each group.

FIG. 3 demonstrates that both creatine and cyclocreatine can protect against increases in levels of salisylate derivatives 2,3 DHBA and 2,5 DHBA after injection of the mitochondrial toxin malonate. This confirms that creatine compounds can indeed protect against production of hydroxyl radicals implicated in oxidative stress and mitochondrial dysfunction. Also FIG. 3 demonstrates that creatine and cyclocreatine have protective effects against nitration of proteins induced by the mitochondrial toxin malonate. Production of nitric oxide and peroxynitrite are part of the cascade of oxidative damage. FIG. 4 illustrates the protective effect of creatine against nitration of proteins induced by another mitochondrial toxin 3-NP.

The conclusion of the experimental results discussed above confirms the importance of the function of the creatine kinase system and the creatine compounds in protecting against cascades of oxidative stress. The process of aging is believed to involve mitochondrial dysfunction and oxidative damage resulting from the production of molecules like hydroxyl radicals, nitric oxide and peroxynitrite. Our results strongly suggest that creatine compounds could indeed minimize damage induced during the process of aging.

Utility

In the present invention, the creatine compounds can be administered to an individual (e.g., a mammal), alone or in combination with another compound, for the prevention or treatment of aging or insult related damage to skin. As agents for skin preservation, creatine compounds can modify creatine kinase/phosphocreatine functions, energy state, oxidative damage, and/or cell survival thereby preventing, ameliorating, arresting or eliminating direct and/or indirect effects of skin damage during aging, exposure to UV radiation, stress, fatigue or other insults. Other compounds which can be administered together with the creatine compounds include antioxidants, vitamins, energy enhancing agents, and other agents used for skin care.

A variety of skin diseases can be treated with creatine or creatine analogs, including but not limited to damage induced during aging or harmful sun radiations. Creatine or analogs of creatine can be used to reduce the severity of damage or inhibit its development. Creatine, creatine phosphate or analogs such as 3-guanidinopropionic acid, guanidino acetate, creatine-pyruvate, creatine ascorbate can be used to treat age related skin damage.

Equivalents

Those skilled in the art will recognize, or be able to ascertain using no more than routine experimentation, many equivalents to the specific embodiments of the invention described herein. Such equivalents are intended to be encompassed by the following claims.

The entire contents of all references, patents, and patent applications cited herein are expressly incorporated by reference.

What is claimed is:

1. A method for treating uneven pigmentation of the skin, comprising administering an composition consisting essentially of an effective amount of a creatine compound and carnitine to a subject, such that said subject is treated for uneven pigmentation of the skin.

2. The method of claim 1, wherein said creatine compound is administered topically or orally.

3. The method of claim 1, wherein said subject is a human.

4. The method of claim 1, wherein said creatine compound is creatine, creatine citrate, creatine ascorbate, cyclocreatine, or creatine phosphate.

5. The method of claim 1, wherein said creatine compound is administered in combination with a pharmaceutically acceptable carrier.

6. The method of claim 5, wherein said pharmaceutically acceptable carrier is suitable for administration as a lotion, cream, mousse, aerosol, gel, emulsion, solution, ointment, or medicated pad.

7. A method for treating uneven pigmentation of the skin, comprising administering a composition consisting essentially of an effective amount of creatine and carnitine to a subject, such that said subject is treated for uneven pigmentation of the skin.

8. The method of claim 7, wherein said creatine is administered topically or orally.

9. The method of claim 7, wherein said subject is a human.

10. The method of claim 7, wherein said creatine is administered in combination with a pharmaceutically acceptable carrier.

11. The method of claim 7, wherein said pharmaceutically acceptable carrier is suitable for administration as a lotion, cream, mousse, aerosol, gel, emulsion, solution, ointment, or medicated pad.

* * * * *